US00PP26927P2

(12) United States Plant Patent
Wood

(10) Patent No.: US PP26,927 P2
(45) Date of Patent: Jul. 12, 2016

(54) LILAC PLANT NAMED 'SMNSYPRZ1'

(50) Latin Name: *Syringa hybrida*
Varietal Denomination: SMNSYPRZ1

(71) Applicant: Timothy D. Wood, Spring Lake, MI (US)

(72) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 14/544,626

(22) Filed: Jan. 23, 2015

(51) Int. Cl.
*A01H 5/00* (2006.01)

(52) U.S. Cl.
USPC ..... Plt./248

(58) Field of Classification Search
USPC ..... Plt./226, 248
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of Lilac plant named 'SMNSYPRZ1', characterized by its upright to outwardly spreading and mounding plant habit; vigorous growth habit; freely branching habit; freely flowering habit; large inflorescences with moderately fragrant lavender purple-colored flowers; long flowering period and remontant flowering habit; and good garden performance.

2 Drawing Sheets

Botanical designation: *Syringa hybrida.*
Cultivar denomination: 'SMNSYPRZ1'.

BACKGROUND OF THE INVENTION

The present invention relates to a new and distinct cultivar of Lilac plant, botanically known as *Syringa hybrida* and hereinafter referred to by the name 'SMNSYPRZ1'.

The new Lilac plant is plant is a product of a planned breeding program conducted by the Inventor in Grand Haven, Mich. The objective of the breeding program is to create new Lilac plants with repeat flowering habit and unique flower colors.

The new Lilac plant originated from an open-pollination in May, 2004 of *Syringa hybrida* 'Josee', not patented, as the female, or seed, parent with an unknown selection of *Syringa hybrida*, not patented, as the male, or pollen, parent. The new Lilac plant was discovered and selected by the Inventor as a single flowering plant from within the progeny of the stated open-pollination in a controlled environment in Grand Haven, Mich. in May, 2007.

Asexual reproduction of the new Lilac plant by softwood to semi-hardwood cuttings in a controlled greenhouse environment in Grand Haven, Mich. since June, 2007 has shown that the unique features of this new Lilac plant are stable and reproduced true to type in successive generations of asexual reproduction.

SUMMARY OF THE INVENTION

Plants of the new Lilac have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNSYPRZ1'. These characteristics in combination distinguish 'SMNSYPRZ1' as a new and distinct Lilac plant:

1. Upright to outwardly spreading and mounding plant habit.
2. Vigorous growth habit.
3. Freely branching habit.
4. Freely flowering habit.
5. Large inflorescences with moderately fragrant lavender purple-colored flowers.
6. Long flowering period and remontant flowering habit.
7. Good garden performance.

Plants of the new Lilac can be compared to plants of the female parent, 'Josee'. Plants of the new Lilac differ primarily from plants of 'Josee' in the following characteristics:

1. Plants of the new Lilac are larger than plants of 'Josee'.
2. Plants of the new Lilac have a stronger reblooming habit than plants of 'Josee'.
3. Plants of the new Lilac and 'Josee' differ in flower color as plants of 'Josee' have lavender pink-colored flowers.

Plants of the new Lilac can be compared to plants of the *Syringa hybrida* 'Palibin', not patented. In side-by-side comparisons conducted in Grand Haven, Mich., plants of the new Lilac differed primarily from plants of 'Palibin' in the following characteristics:

1. Plants of the new Lilac were larger than plants of 'Palabin'.
2. Plants of the new Lilac had a stronger reblooming habit than plants of 'Palabin'.
3. Plants of the new Lilac and 'Palibin' differed in flower color as plants of 'Palabin' had light pink-colored flowers.
4. Flower color of plants of the new Lilac did not fade whereas flower color of plants of 'Palabin' faded to white.

Plants of the new Lilac can be also compared to plants of the *Syringa hybrida* 'Penda', disclosed in U.S. Plant Pat. No. 20,575. In side-by-side comparisons conducted in Grand Haven, Mich., plants of the new Lilac differed primarily from plants of 'Penda' in the following characteristics:

1. Plants of the new Lilac were larger than plants of 'Penda'.
2. Plants of the new Lilac were more resistant to *Pseudomonas syringae* than plants of 'Penda'.

BRIEF DESCRIPTION OF THE PHOTOGRAPHS

The accompanying colored photographs illustrate the overall appearance of the new Lilac plant showing the colors as true as it is reasonably possible to obtain in colored reproductions of this type. Colors in the photographs may differ slightly from the color values cited in the detailed botanical description which accurately describe the colors of the new Lilac plant.

The photograph on the first sheet is a side perspective view of a flowering typical plant of 'SMNSYPRZ1' grown in an outdoor nursery in early summer.

The photograph on the second sheet is a close-up view of a typical flowering typical plant of 'SMNSYPRZ1'.

Plants used for the photographs were four years old.

DETAILED BOTANICAL DESCRIPTION

Plants used for the following description were grown during the spring and early summer in three-gallon containers in a polypropylene-covered shadehouse in Grand Haven, Mich. and under cultural practices typical of commercial Lilac production. During the production of the plants, day temperatures ranged from 18° C. to 27° C. and night temperatures ranged from 5° C. to 10° C. Plants of the new Lilac were two years old when the description was taken. Plants were overwintered in a polyethylene-covered greenhouse. In the following description, color references are made to The Royal Horticultural Society Colour Chart, 1995 Edition, except where general terms of ordinary dictionary significance are used.

Botanical classification: *Syringa hybrida* 'SMNSYPRZ1'.

Parentage:

- *Female, or seed, parent.*—*Syringa hybrida* 'Josee', not patented.
- *Male, or pollen, parent.*—Unknown selection of *Syringa hybrida*, not patented.

Propagation:

- *Type.*—By softwood to semi-hardwood cuttings.
- *Time to initiate roots, summer.*—About 18 days at 27° C.
- *Time to produce a rooted young plant, summer.*—About three months at 27° C.
- *Root description.*—Fine, fibrous.
- *Rooting habit.*—Freely branching; dense.

Plant description:

- *Plant form and growth habit.*—Perennial shrub; upright to outwardly spreading and mounding plant habit; vigorous growth habit.
- *Branching habit.*—Freely branching habit, about seven lateral branches develop per plant.
- *Plant height.*—About 61 cm.
- *Plant diameter (area of spread).*—About 53 cm.

Lateral branch description:

- *Length.*—About 60 cm.
- *Diameter.*—About 2 mm.
- *Internode length.*—About 2 cm to 2.5 cm.
- *Aspect.*—Erect to about 20° from vertical.
- *Strength.*—Strong.
- *Texture, developing.*—Slightly pubescent.
- *Texture, developed.*—Smooth, glabrous.
- *Color, developing.*—Between 147B and 197A; distally, tinted with close to 182B; upper surface, tinted with close to 183A.
- *Color, developed.*—Close to 199A.

Leaf description:

- *Arrangement.*—Opposite, simple.
- *Length.*—About 2.5 cm.
- *Width.*—About 1.5 cm to 2 cm.
- *Shape.*—Broadly ovate.
- *Apex.*—Acute to cuspidate.
- *Base.*—Obtuse.
- *Margin.*—Entire; slightly ciliate.
- *Texture, upper and lower surfaces.*—Slightly pubescent.
- *Venation pattern.*—Pinnate.
- *Color.*—Developing and fully expanded leaves, upper surface: Close to 137A; venation, close to 137A. Developing and fully expanded leaves, lower surface: Close to 137C; venation, close to 137C.
- *Petioles.*—Length: About 5 mm. Diameter: About 0.5 mm. Texture, upper and lower surfaces: Smooth, glabrous. Color, upper surface: Close to 138A. Color, lower surface: Close to 138B.

Flower description:

- *Flower arrangement and flowering habit.*—Single salverform flowers arranged in terminal panicles; freely flowering habit with usually about 450 flowers developing per inflorescence; flowers face upright to outwardly.
- *Natural flowering season and flower longevity.*—Long flowering period; plants of the new Lilac flower from spring until autumn in Grand Haven, Mich.; remontant flowering habit, plants flower in May and reflower again in July, continuing to flower until frost; flowers not persistent.
- *Fragrance.*—Moderately fragrant; fragrance sweet and pleasant.
- *Inflorescence height.*—About 7 cm to 12 cm.
- *Inflorescence diameter.*—About 8 cm to 12 cm.
- *Flower diameter.*—About 7 mm.
- *Flower length (height).*—About 1.1 cm.
- *Flower buds.*—Length: About 9 mm. Diameter: About 2 mm. Shape: Obovate. Color: Close to 77A.
- *Petals.*—Quantity and arrangement: Single whorl of four petals; lower portion of petals fused forming a narrow tube. Lobe length: About 3 mm. Lobe width: About 2 mm. Lobe shape: Ovate. Apex: Acute; slightly cupped. Margin: Entire. Texture, upper and lower surfaces: Smooth, glabrous. Color: When opening and fully opened, upper surface: Close to 76A; color does not fade with development. When opening and fully opened, lower surface: Close to 82B; color does not fade with development.
- *Sepals.*—Quantity and arrangement: Single whorl of five small sepals; fused towards the base forming a campanulate-shaped calyx. Length: Less than 1 mm. Width: Less than 1 mm. Shape: Oblanceolate. Apex: Acute. Margin: Entire. Texture, upper and lower surfaces: Smooth, glabrous. Color, upper and lower surfaces: Close to 137A.

*Peduncles*.—Length: About 9 cm. Diameter: About 1 mm. Strength: Strong. Aspect: Upright to outwardly. Texture: Smooth, glabrous. Color: Close to 145A.

*Pedicels*.—Length: About 2 mm to 3 mm. Diameter: About 0.5 mm. Strength: Strong. Aspect: Upright to outwardly. Texture: Smooth, glabrous. Color: Close to 145A.

*Reproductive organs*.—Androecium: Quantity of stamens per flower: Two. Anther shape: Oblong. Anther length: About 2 mm. Anther color: Close to 201A. Amount of pollen: Scarce. Pollen color: Close to 1A. Gynoecium: Quantity of pistils per flower: One. Pistil length: About 3 mm. Style length: About 2 mm. Style color: Close to 155A. Stigma shape: Oblong to rounded. Stigma color: Close to 155A.

*Seeds and fruits*.—Seed and fruit development have not been observed on plants of the new Lilac.

Garden performance: Plants of the new Lilac have been observed to have good garden performance and to tolerate rain, wind and temperatures ranging from about −31° C. to about 38° C.

Pathogen & pest resistance: Plants of the new Lilac have been observed to be resistant to *Pseudomonas syringae* and powdery mildew. Plants of the new Lilac have not been shown to be resistant to pests and other pathogens common to Lilac plants.

It is claimed:

1. A new and distinct Lilac plant named 'SMNSYPRZ1' as illustrated and described.

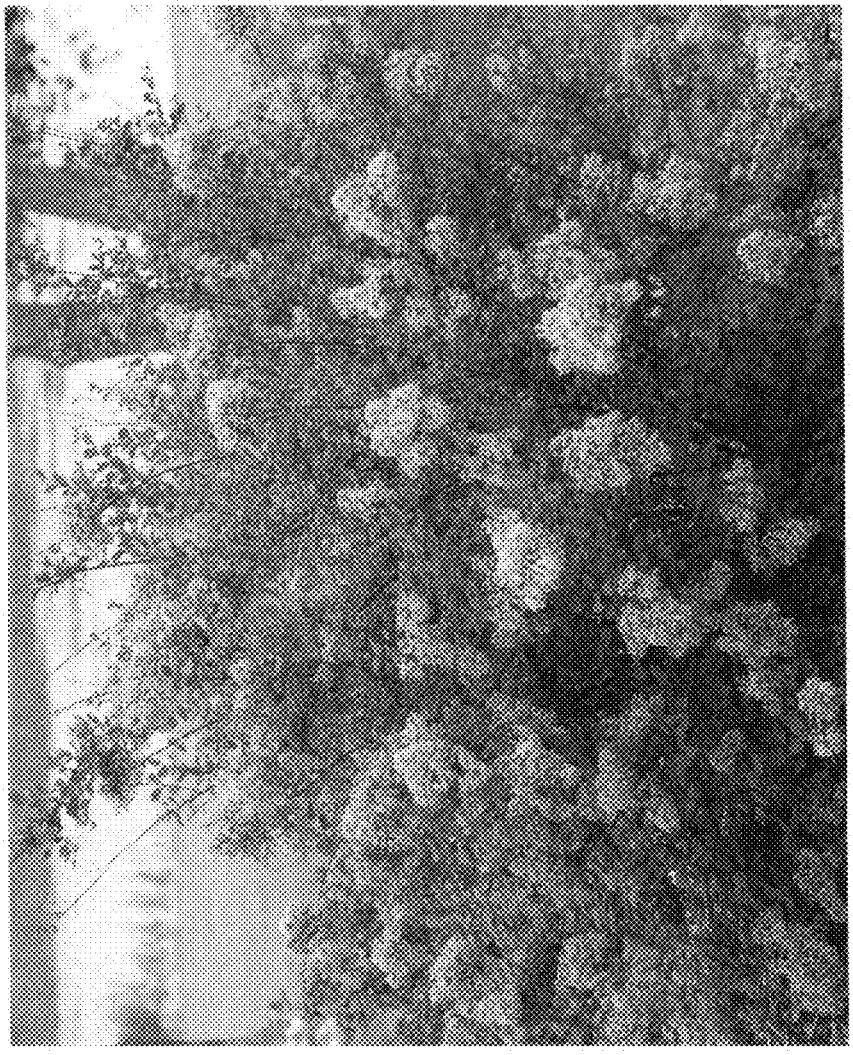

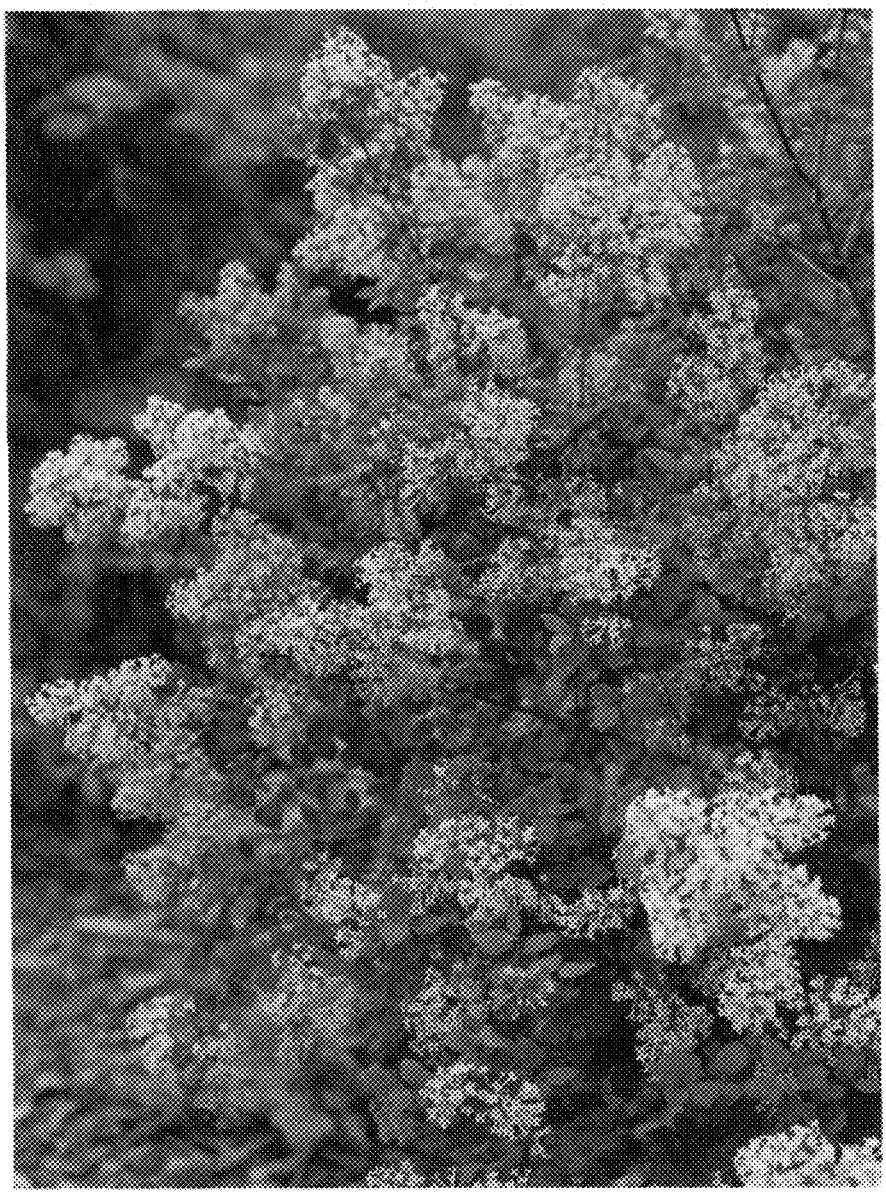

* * * * *